(12) United States Patent
Hong et al.

(10) Patent No.: US 8,237,930 B2
(45) Date of Patent: Aug. 7, 2012

(54) OXYGEN SENSOR USING PRINCIPLE OF SURFACE PLASMON RESONANCE AND OXYGEN TRANSMISSION RATE MEASUREMENT SYSTEM INCLUDING THE SAME

(75) Inventors: Jae Min Hong, Seoul (KR); Hee Dok Choi, Inchun (KR); Il Doo Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 390 days.

(21) Appl. No.: 12/543,343

(22) Filed: Aug. 18, 2009

(65) Prior Publication Data
US 2010/0045997 A1 Feb. 25, 2010

(30) Foreign Application Priority Data
Aug. 21, 2008 (KR) .................. 10-2008-0082034

(51) Int. Cl.
*G01N 21/55* (2006.01)
*G01N 21/00* (2006.01)
*G01N 17/00* (2006.01)
*G01J 4/00* (2006.01)

(52) U.S. Cl. ................ 356/445; 356/369; 422/82.05; 422/91

(58) Field of Classification Search ................ None
See application file for complete search history.

(56) References Cited

U.S. PATENT DOCUMENTS

| 4,844,613 | A | | 7/1989 | Batchelder et al. |
| 4,889,427 | A | | 12/1989 | Van Veen et al. |
| 5,359,681 | A | | 10/1994 | Jorgenson et al. |
| 6,001,067 | A | * | 12/1999 | Shults et al. .................. 600/584 |
| 6,067,840 | A | | 5/2000 | Chelvayohan et al. |
| 6,460,405 | B1 | | 10/2002 | Mayer et al. |
| 6,567,753 | B2 | * | 5/2003 | Potyrailo ...................... 702/39 |
| 6,752,962 | B2 | * | 6/2004 | Carr et al. ................ 422/82.05 |
| 7,864,322 | B2 | * | 1/2011 | Carpenter et al. ............ 356/437 |
| 2005/0087452 | A1 | * | 4/2005 | McAnalley et al. ........ 205/777.5 |

* cited by examiner

*Primary Examiner* — Hwa Lee
*Assistant Examiner* — Gordon Stock, Jr.
(74) *Attorney, Agent, or Firm* — LRK Patent Law Firm

(57) ABSTRACT

Provided is an oxygen sensor using surface plasmon resonance, including: a laser diode emitting light; a polarizer converting the emitted light into polarized light; a prism receiving the polarized light from the polarizer and having a sensor substrate on one surface thereof so that the polarized light is reflected, the sensor substrate coated with oxygen-sensitive organic material; an oxygen concentration measurement chamber provided to enclose the sensor substrate so that oxygen whose concentration is to be measured is contained therein; a photodiode measuring an amount of light reflected from the prism; and a microcontroller unit controlling operation of the oxygen sensor and calculating the oxygen concentration. Further, the oxygen concentration is determined using the microcontroller unit having absolute concentrations corresponding to the amount of light measured using the photodiode, and the oxygen concentration is measured where an incidence angle of the polarized light incident on the sensor substrate is fixed.

31 Claims, 7 Drawing Sheets

OXYGEN SENSOR USING PRINCIPLE OF SURFACE PLASMON RESONANCE AND OXYGEN TRANSMISSION RATE MEASUREMENT SYSTEM INCLUDING THE SAME

BACKGROUND OF THE INVENTION

1. Field of the Invention

The present invention relates to an oxygen sensor using the principle of surface plasmon resonance (SPR) and an oxygen transmission rate (OTR) measurement system including the oxygen sensor.

2. Description of the Related Art

With the recent development of displays in terms of materials and structures, the demand for sensors having functions which have not been provided before is increasing. In this regard, there is exemplified an organic light emitting device (OLED) as a flat display. The OLED is receiving attention as a next-generation display which is solely for emitting light. The display includes materials and structures having electrical, mechanical and optical properties. In the OLED, organic material may cause a danger of impairment attributable to reaction with water vapor and oxygen. Thus, because the OLED must maximally block out water vapor and oxygen which have a direct influence on the lifespan thereof, a highly blockable substrate, a sealing material, and an enclosing material or the like is employed.

Hence, as the evaluation of a material or structure having a very low gas transmission rate is required, methods therefor have been developed. The measurement of the transmission rate of the material and structure requires a measurement tool having high sensitivity, in particular, a gas sensor able to evaluate a very low gas transmission rate.

As an example of the sensor, an IR gas sensor is disclosed in U.S. Pat. No. 6,067,840 granted to Texas Instruments Inc. To determine the concentration of gas to be monitored, differential absorption between two IR sources respectively disposed toward a sensing gas and a reference gas is applied. As another example, U.S. Pat. No. 6,460,405 granted to MOCON, Inc. discloses a gas sensor, in which a measuring sample is exposed to a chemically inert tracer gas such as helium or carbon dioxide, and which includes a tracer gas detector for measuring the flow of tracer gas through the sample, the measured value being related to a gas transmission rate of the experimental sample.

With regard to SPR useful in the present invention and quite different from the above techniques, general SPR-based sensors including a transparent prism and a metal film applied to a thickness of about 50 nm thereon and methods of measuring changes in the dielectric constant or refractive index corresponding to changes in a sample on the metal film have been proposed. First, U.S. Pat. No. 4,889,427 discloses a method of measuring a resonance angle and its change while changing an incidence angle θ using the incident light of a monochromatic light source and a prism having a predetermined refractive index.

Second, U.S. Pat. No. 5,359,681 discloses a method of measuring changes in wavelength depending on resonance conditions using a light source having multiple wavelengths including white light at an incidence angle θ within a limited range.

Third, U.S. Pat. No. 4,844,613 discloses a method of measuring a resonance angle without a rotational driver using a multi-channel light receiving device such as a photodiode array (PDA) while a light source of an expanded single wavelength is focused on the center of a medium.

These days, techniques using local surface plasmon effects occurring not with a metal film but with metal nanoparticles have been devised. In the case where the metal nanoparticles are dispersed in a dielectric material, local field enhancement occurs due to SPR caused by the metal nanoparticles, resulting in very large optical nonlinearity.

The use of a glass substrate for a microscope coated with metal nanoparticles as a sensor substrate includes T-LSPR (Transmission Localized Surface Plasmon Resonance Spectroscopy) or P-SPR (Propagating Surface Plasmon Resonance Spectroscopy) As such, T-LSPR employs a sensor including a transparent substrate coated considerably thinly with a film or metal nanoparticles. T-LSPR shares the same basic principle as that of P-SPR with the exception that the sensor substrate is manufactured slightly differently, and is used to measure, using a UV-visible spectrometer, changes around the sensor based on changes in SPR absorption coefficient after application of an oxygen-sensitive organic material on the sensor substrate including transparent glass coated with metal nanoparticles.

SUMMARY OF THE INVENTION

Accordingly, the present invention provides a selective measurement method using a principle different from the principle of the aforementioned oxygen sensors and OTR measurement systems. In the conventional techniques, a selective oxygen-sensitive material has been used, but the use of the principle of SPR cannot be found.

Whereas OTR is conventionally measured not through a direct method but through an indirect method, in the present invention, direct measurement of only oxygen gas is possible. Typically, a sensor using surface resonance, which has been used in various fields, is able to mainly measure materials in the solid and liquid states. However, in the present invention, the concentration of oxygen gas is measured using the principle of SPR in a manner such that an oxygen-sensitive material (an organic material including a metal-porphyrin such as hemin or hemoglobin) for adsorbing or desorbing oxygen is applied on a transparent substrate such as glass coated very thinly with a metal film or nanoparticles, so that field enhancement effects are induced by the metal, thus detecting a reflection signal, thereby measuring a resonance angle depending on the concentration of oxygen in the space around the sensor. Furthermore, according to the present invention, the substrate for the oxygen sensor can be easily mass produced at low cost, and the concentration of oxygen can be monitored in real time.

In addition, the present invention provides a new and improved measurement method which measures only the change in voltage depending on the concentration of oxygen in a state in which an angle is fixed at an appropriate position of a resonance curve, unlike conventional SPR measurement methods of measuring changes in angle and wavelength. Compared to conventional methods of measuring an angle change at various angles, in the present invention, an angle is fixed at a certain value, and thus the measurement time becomes shortened. Also, in the present invention, a single wavelength light source is used. When the light source is fixed at an angle causing the largest change in the resonance curve, the measuring speed of the measurement system may become faster and the system simplified and miniaturized.

Because the oxygen sensor according to the present invention is capable of measuring the state of the oxygen-sensitive organic material depending on the oxygen concentration, it is simply and easily usable and its substrate is economically manufactured. Also, the sensor using SPR is necessary for the development of the OTR measurement system.

A first aspect of the present invention is to provide an oxygen sensor using the principle of SPR, including a laser diode for emitting light; a polarizer for converting light emitted from the laser diode into polarized light; a prism for receiving the polarized light from the polarizer and having a sensor substrate provided on one surface thereof so that the polarized light is reflected, the sensor substrate being coated with an oxygen-sensitive organic material; an oxygen concentration measurement chamber provided to enclose the sensor substrate so that oxygen a concentration of which is to be measured is contained therein; a photodiode for measuring an amount of light reflected from the prism; and a microcontroller unit for controlling the operation of the oxygen sensor and calculating the oxygen concentration, wherein the oxygen concentration is determined using the microcontroller unit having values of absolute concentration corresponding to the amount of light measured using the photodiode, and the oxygen concentration is measured in a state in which an incidence angle of the polarized light incident on the sensor substrate is fixed.

In the first aspect, the oxygen sensor may further include a pressure measurement pipe, one side of which is connected to the oxygen concentration measurement chamber and the other side of which is connected to a vacuum pump and which includes a pressure gauge provided on an upper surface thereof and a vacuum pump valve disposed between the pressure gauge and the vacuum pump; and a gas input pipe, one side of which is connected to the oxygen concentration measurement chamber and the other side of which is connected to a gas input valve.

In the first aspect, the sensor substrate may include a dielectric substrate; a nano-metal layer including metal nanoparticles applied on the dielectric substrate; and an organic material layer formed by linking the organic material to the metal nanoparticles of the nano-metal layer.

In the first aspect, the sensor substrate may include a dielectric substrate; a nano-metal layer including a metal film applied on the dielectric substrate; and an organic material layer formed on the nano-metal layer.

In the first aspect, the organic material may be responsible for either or both of adsorption and desorption of oxygen gas.

In the first aspect, the organic material may be a metal-porphyrin or hemoglobin which is selectively sensitive to only oxygen.

In the first aspect, the metal nanoparticles may have a diameter ranging from 1 nm to 99 nm.

In the first aspect, the dielectric substrate may be made of an optical material, such as glass, which is transparent to light in the visible range.

In the first aspect, the metal film may be made of a metal or a metal-added inorganic or organic material.

In the first aspect, the oxygen sensor may further include a measurement chamber guide disposed to enclose the oxygen concentration measurement chamber.

A second aspect of the present invention provides an OTR measurement system including an oxygen sensor using the principle of SPR, the OTR measurement system being composed of the oxygen sensor including a laser diode for emitting light, a polarizer for converting light emitted prom the laser diode into polarized light, a prism for receiving the polarized light from the polarizer and having a sensor substrate provided on one surface thereof so that the polarized light is reflected, the sensor substrate being coated with an oxygen-sensitive organic material, an oxygen concentration measurement chamber provided to enclose the sensor substrate so that oxygen a concentration of which is to be measured is contained therein, a photodiode for measuring an amount of light reflected from the prism, and a microcontroller unit for controlling operation of the oxygen sensor and calculating an oxygen concentration change and an OTR; and an oxygen supplier connected to one side of the oxygen sensor to supply oxygen gas, wherein the OTR is measured by determining the oxygen concentration change from the amount of the light measured using the photodiode at predetermined temporal intervals.

In the second aspect, the oxygen supplier may include a gas input pipe one side of which is connected to the oxygen concentration measurement chamber and the other side of which is connected to a gas input valve; a sample mounting device one side of which is connected to the gas input valve and the other side of which is connected to an oxygen supply valve; and an oxygen gas supplier one side of which is connected to the oxygen supply valve.

In the second aspect, the sensor substrate may include a dielectric substrate; a nano-metal layer including metal nanoparticles applied on the dielectric substrate; and an organic material layer formed by linking the organic material to the metal nanoparticles of the nano-metal layer.

In the second aspect, the sensor substrate may include a dielectric substrate; a nano-metal layer including a metal film applied on the dielectric substrate; and an organic material layer formed on the nano-metal layer.

In the second aspect, the organic material may be responsible for either or both of adsorption and desorption of oxygen gas.

In the second aspect, the organic material may be a metal-porphyrin or hemoglobin which is selectively sensitive to only oxygen.

In the second aspect, the metal nanoparticles may have a diameter ranging from 1 nm to 99 nm.

In the second aspect, the metal film may have a thickness ranging from 1 nm to 99 nm.

In the second aspect, the dielectric substrate may be made of an optical material, such as glass, which is transparent to light in the visible range.

In the second aspect, the metal film may be made of a metal or a metal-added inorganic or organic: material.

In the second aspect, the sample mounting device may include an oxygen sensor connection pipe one side of which is connected to the gas input valve; a second transmission rate measurement block through which the oxygen sensor connection pipe perforates and having a recess formed in one side thereof; a porous metal layer both side surfaces of which are in contact with the recess of the second transmission rate measurement block; a transmission rate measurement sample a lower surface of which is in contact with the porous metal layer and the second transmission rate measurement block; a first transmission rate measurement block disposed symmetrically to the second transmission rate measurement block; a circular O-ring disposed at both sides between the first transmission rate measurement block and the second transmission rate measurement block to support the first transmission rate measurement block and the second transmission rate measurement block; and a gas supply pipe having a cylindrical shape, which is perforated through the first transmission rate measurement block and connected to a center of an upper surface of the first transmission rate measurement block.

DESCRIPTION OF SPECIFIC EMBODIMENTS

Figure 1:
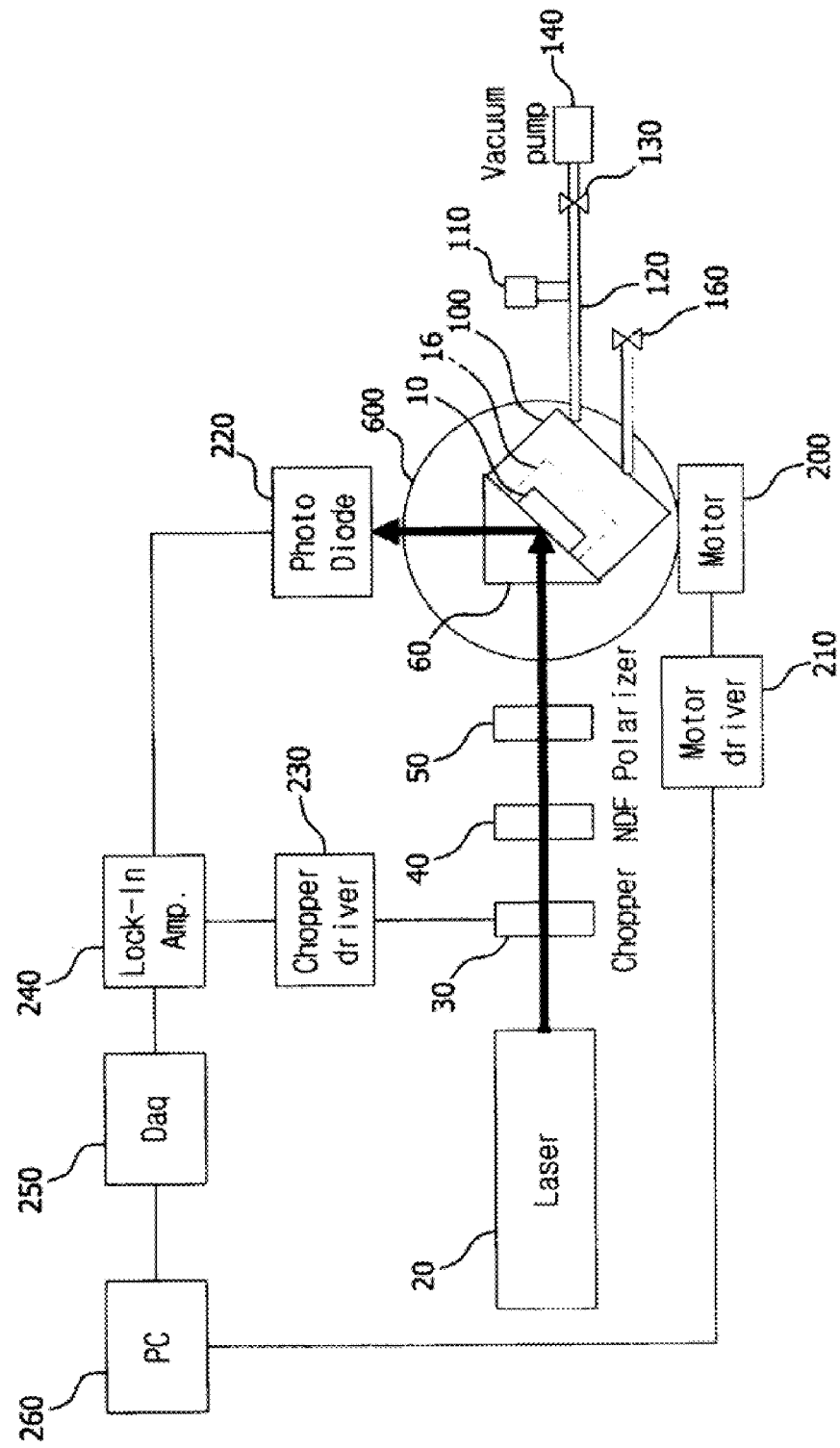
FIG. 1 schematically shows the entire configuration of an oxygen sensor for measuring an oxygen concentration to determine a resonance angle.

Hereinafter, a detailed description will be given of constructions and effects of embodiments of the present invention with reference to the appended drawings.

In an embodiment, an oxygen sensor 530 using the principle of SPR, according to the present invention, includes a laser diode 510 for emitting light; a polarizer 50 for converting light emitted from the laser diode 510 into polarized light; a prism 60 for receiving the polarized light from the polarizer and having a sensor substrate 10 provided on one surface thereof so that the polarized light is reflected, the sensor substrate being coated with an oxygen-sensitive organic material; an oxygen concentration measurement chamber 16 provided to enclose the sensor substrate so that oxygen a concentration of which is to be measured is contained therein; a measurement chamber guide 100; a photodiode 220 for measuring an amount of light reflected from the prism; and a microcontroller unit 500 for controlling the operation of the oxygen sensor and calculating the oxygen concentration, wherein the oxygen concentration is determined using the microcontroller unit 500 having values of absolute concentration corresponding to the amount of light measured using the photodiode 220, and the oxygen concentration is measured in a state in which an incidence angle of the polarized light incident on the sensor substrate is fixed.

The oxygen sensor 530 further includes a pressure measurement pipe 120, one side of which is connected to the oxygen concentration measurement chamber 16 and the other side of which is connected to a vacuum pump 140 and which includes a pressure gauge 110 provided on an upper surface thereof and a vacuum pump valve 130 disposed between the pressure gauge 110 and the vacuum pump 140; and a gas input pipe 150, one side of which is connected to the oxygen concentration measurement chamber 16 and the other side of which is connected to a gas input valve.

The sensor substrate 10 includes a dielectric substrate 11; a nano-metal layer 540 including metal nanoparticles applied on the dielectric substrate; and an organic material layer 550 formed by linking the organic material to the metal nanoparticles of the nano-metal layer 540.

The sensor substrate 10 includes a dielectric substrate 11; a nano-metal layer including a metal film applied on the dielectric substrate; and an organic material layer 550 formed on the nano-metal layer.

The organic material is responsible for either or both of adsorption and desorption of oxygen gas.

The organic material is a metal-porphyrin or hemoglobin which is selectively sensitive to only oxygen.

The metal nanoparticles have a diameter ranging from 1 nm to 99 nm.

The dielectric substrate 11 is made of an optical material, such as glass, which is transparent to light in the visible range.

The metal film is made of a metal or a metal-added inorganic or organic material.

The oxygen sensor 530 further includes a measurement chamber guide disposed to enclose the oxygen concentration measurement chamber.

In a second embodiment, an OTR measurement system including an oxygen sensor using the principle of SPR according to the present invention is composed of the oxygen sensor including a laser diode 510 for emitting light, a polarizer 50 for converting light emitted from the laser diode into polarized light, a prism 60 for receiving the polarized light from the polarizer and having a sensor substrate 10 provided on one surface thereof so that the polarized light is reflected, the sensor substrate being coated with an oxygen-sensitive organic material, an oxygen concentration measurement chamber 16 provided to enclose the sensor substrate so that oxygen a concentration of which is to be measured is contained therein, a photodiode 220 for measuring an amount of light reflected from the prism, and a microcontroller unit 500 for controlling operation of the oxygen sensor and calculating an oxygen concentration change and an OTR; and an oxygen supplier connected to one side of the oxygen sensor to supply oxygen gas, wherein the OTR is measured by determining the oxygen concentration change from the amount of the light measured using the photodiode 220 at predetermined temporal intervals.

The oxygen supplier includes a gas input pipe 150 one side of which is connected to the oxygen concentration measurement chamber 16 and the other side of which is connected to a gas input valve 160; a sample mounting device 300 one side of which is connected to the gas input valve 160 and the other side of which is connected to an oxygen supply valve 411 with oxygen gas input pipe 310; and an oxygen gas supplier 410 one side of which is connected to the oxygen supply valve.

The sensor substrate 10 includes a dielectric substrate 11; a nano-metal layer 540 including metal nanoparticles applied on the dielectric substrate; and an organic material layer 550 formed by linking the organic material to the metal nanoparticles of the nano-metal layer.

The sensor substrate 10 includes a dielectric substrate 11; a nano-metal layer 540 including a metal film applied on the dielectric substrate; and an organic material layer 550 formed on the nano-metal layer.

The organic material is responsible for either or both of adsorption and desorption of oxygen gas.

The organic material is a metal-porphyrin or hemoglobin which is selectively sensitive to only oxygen.

The metal nanoparticles have a diameter ranging from 1 nm to 99 nm.

The metal film has a thickness ranging from 1 nm to 99 nm.

The dielectric substrate 11 is made of an optical material, such as glass, which is transparent to light in the visible range.

The metal film is made of a metal or a metal-added inorganic or organic material.

The sample mounting device 300 includes an oxygen sensor connection pipe 360 one side of which is connected to the gas input valve 160; a second transmission rate measurement block 390 through which the oxygen sensor connection pipe 360 perforates and having a recess formed in one side thereof; a porous metal layer 340 both side surfaces of which are in contact with the recess of the second transmission rate measurement block 390; a transmission rate measurement sample 350 a lower surface of which is in contact with the porous metal layer 340 and the second transmission rate measurement block 390; a first transmission rate measurement block 320 disposed symmetrically to the second transmission rate measurement block 390; a circular O-ring 330 disposed at both sides between the first transmission rate measurement block 320 and the second transmission rate measurement block 390 to support the first transmission rate measurement block 320 and the second transmission rate measurement block 390; and a gas supply pipe 310 having a cylindrical shape, which perforates through the first transmission rate measurement block 320 and connected to the center of the upper surface of the first transmission rate measurement block 320; a gas include oxygen 380 from an oxygen gas supplier 410 go by a gas supply pipe 310; and a transmission gas 370 through sample mounting device 300.

The present invention pertains to selective measurement of concentration of only oxygen in a gas and provides an OTR measurement system. To this end, an oxygen-sensitive organic material is used and SPR well-known in the art is employed. When the oxygen-sensitive organic material is applied on a metal-deposited substrate, the refractive index changes because of the interaction of the material in response to the sensitivity to oxygen, resulting in changes in SPR. For reaction at an interface between the metal and the material (which is sensitive to oxygen), resonance conditions may vary depending on the state (refractive index or thickness) of the material in contact with the metal. In the case where light having a predetermined wavelength is incident under certain resonance conditions, an angle at which resonance efficiently occurs is determined at the interface between the metal and the material. Thus, in the case of a resonance angle, incident light is used for resonance and thus reflectivity thereof is reduced. Consequently, the refractive index may be variously induced depending on the type of oxygen-sensitive material and the kind of interaction, and such changes in refractive index are measured, thereby determining the concentration and properties of oxygen around the sensor substrate.

On a substrate coated very thinly with a metal film or metal nanoparticles, which may be mass produced at low cost, an oxygen-sensitive organic material is applied, after which the optically induced resonance angle or refractive index is monitored using SPR, thereby facilitating the arrangement of optical systems including a prism, an optical rotator and an spectrometer and measuring a signal denoting the concentration of oxygen.

The sensor sample which is selectively sensitive only to oxygen may include an organic material including a metal-porphyrin such as hemin or hemoglobin responsible for either or both of adsorption and desorption of oxygen depending on the spatial conditions thereof.

The sensor is provided with a resonance angle measurement device based on SPR, so as to determine a resonance angle change depending on the concentration of oxygen in the chamber of the sensor containing the sensor sample.

Figure 3:
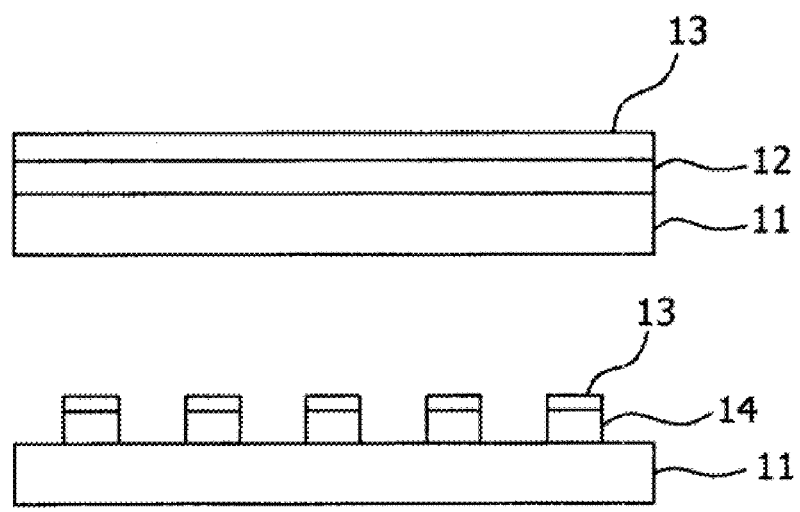
FIG. 3 schematically shows a sensor substrate including a monolayer metal film and a sensor substrate including a thin nanoparticle film according to embodiments of the present invention.

FIG. 3 schematically shows a sensor substrate including a monolayer metal film 12 and a sensor substrate including a thin nanoparticle film 14 according to embodiments of the present invention.

As shown in FIG. 3, the sensor substrate is configured such that metal nanoparticles and an oxygen-sensitive organic material 13 are sequentially applied on a dielectric substrate. Alternatively, the sensor substrate may be configured such that a metal film and an oxygen-sensitive organic material are sequentially applied on a dielectric substrate. The case where the metal film is applied is described below.

To this end, glass as a dielectric substrate is first prepared, after which Ti 2~5 nm thick and Au 40 nm thick are sequentially deposited on glass. The reason why Ti is deposited is to increase adhesiveness between glass which is a dielectric and Au which is a metal. As such, Au may be deposited to a thickness adapted to cause a maximum change in measured value when the oxygen-sensitive organic material is deposited.

Alternatively, the case where the metal nanoparticles are applied is described below. To this end, Ti 2~5 nm thick and a metal nanoparticle layer are sequentially deposited on glass used as the dielectric substrate. The reason why Ti is deposited is to increase adhesiveness between glass which is a dielectric and the metal nanoparticle layer. The metal nanoparticle layer is deposited to a thickness adapted to cause a maximum change in measured value when the oxygen-sensitive organic material is deposited.

Next, the oxygen-sensitive organic material is applied on the substrate. For example, hemin which adsorbs and desorbs oxygen may be deposited on the substrate prepared as above using a thermal evaporation system. As such, an experiment for controlling the thickness of hemin to be deposited should be preliminary conducted. The thickness of hemin may be controlled depending on the amount of hemin used for the deposition and the deposition time.

Figure 7:
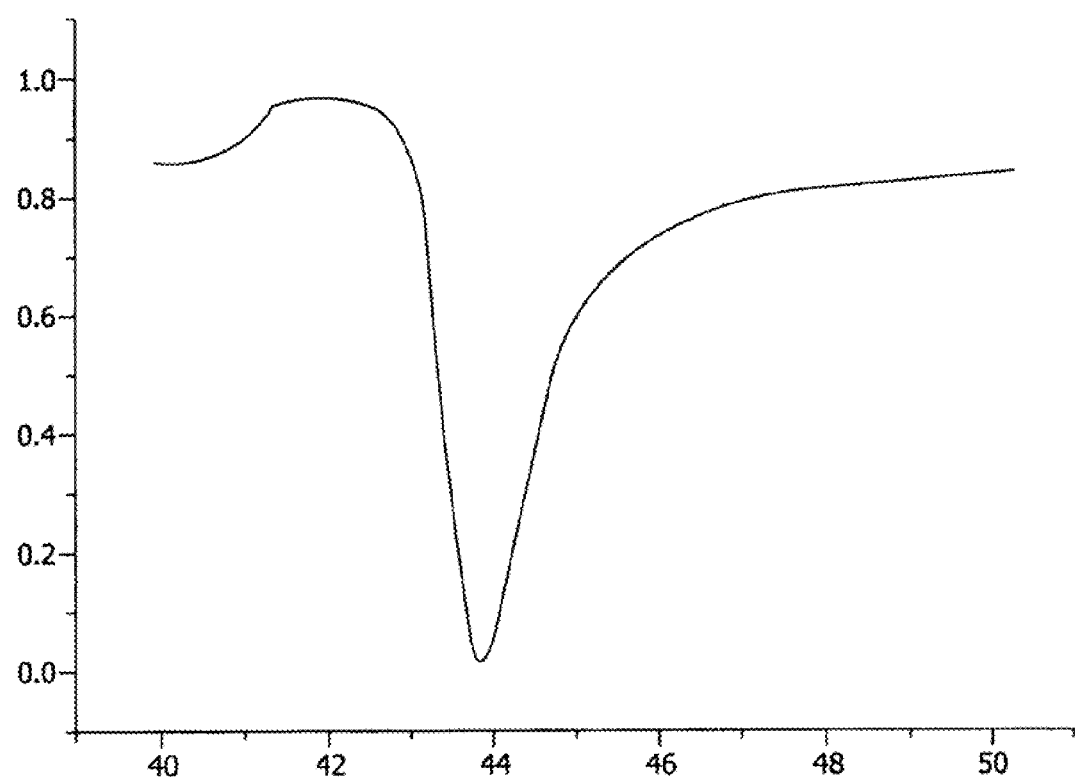
FIG. 7 shows the reflectivity depending on the angle.

Next, measurement of the resonance angle using SPR is carried out. FIG. 1 schematically shows the entire configuration of the oxygen sensor for measuring the concentration of oxygen to determine the resonance angle. When a single-wavelength laser source 20 is incident on the metal film or metal particles through the prim 60, an incident angle about metal film, an incident laser modulated by chopper 30, controlled intensity by Neutral Density Filter (NDF) 40, part of the laser is reflected, and the other part thereof is used to generate SPR between the metal film and the dielectric material. A chopper 30 is controlled by chopper driver 230. When the angle at which surface plasmon is greatly generated is determined depending on the angle of incident laser, light is mainly used for the production of plasmon while the amount of reflected light is reduced. The amount of reflected laser is measured using the photodiode 220 and signals of photodiode 220 collect with data acquisition 250 and send to PC 260. Because only data corresponding to the frequency to be chopped using a lock-in amplifier 240 is received, almost all noise is reduced, and desired data may be obtained in an amplified state. Furthermore, only the laser polarized to P waves using the polarizer 50 is incident. As such, S waves are ineffectual and are thus excluded. In this state, desired values may be gained at a single angle which is fixed. When predetermined values are fed to the photodiode 220 in conjunction with rotation of a rotator 600 which rotated by motor 200 with motor driver 210, main control PC 260, reflectivity depending on the angle may be measured, thus obtaining the data as shown in FIG. 7. The data of FIG. 7 shows reflectivity, and the angle corresponding to the minimum point of the lower portion of the reflectivity curve is referred to as the resonance angle.

In order to measure the change in the resonance angle according to the embodiment of the present invention, the principle of SPR is employed. As such, the total reflection angle using the principle and the SPR signal of Au itself were confirmed before the embodiment.

The sensor substrate prepared as above is attached to the prism. In order to minimize the difference in refractive index, index matching oil is used. The prism, the index matching oil and the glass which is the dielectric substrate are used at the same refractive index.

Figure 4:
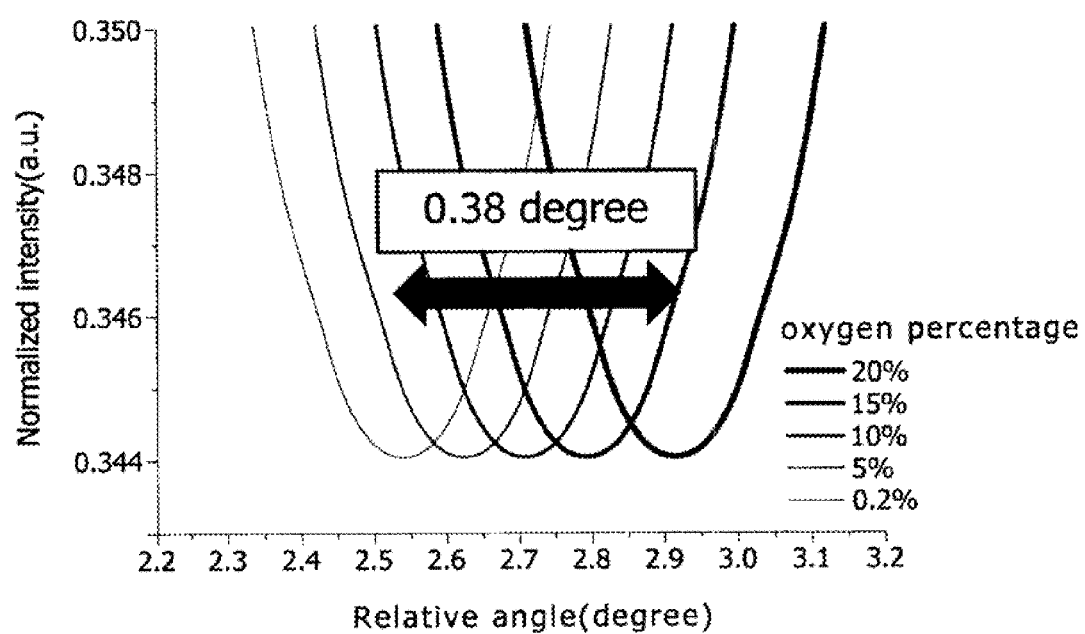
FIG. 4 shows the measured values using the monolayer metal film according to the embodiment of the present invention.

The change in the oxygen concentration of the sensor substrate is controlled by adjusting the pressure of a measurement chamber. The change in SPR angle depending on the oxygen concentration thus controlled is measured. The results are shown in FIG. 4. The relative angle is an angle with respect to a position at which measurement begins. Actually, the value of a physically absolute position is insignificant, and thus is not used. This is because only the relative angle shift is considered important. For example, the relative angle shift of 0.38 degrees is regarded as important. FIG. 4 shows the lower portions of resonance angle curves measured by controlling the oxygen concentration around the sensor material to 0.2%, 5%, 10%, 15% and 20%. Specifically, FIG. 4 shows the lower portions of five resonance angle curves depending on circumferences, as in the graph (resonance curve) of FIG. 7.

Figure 5:
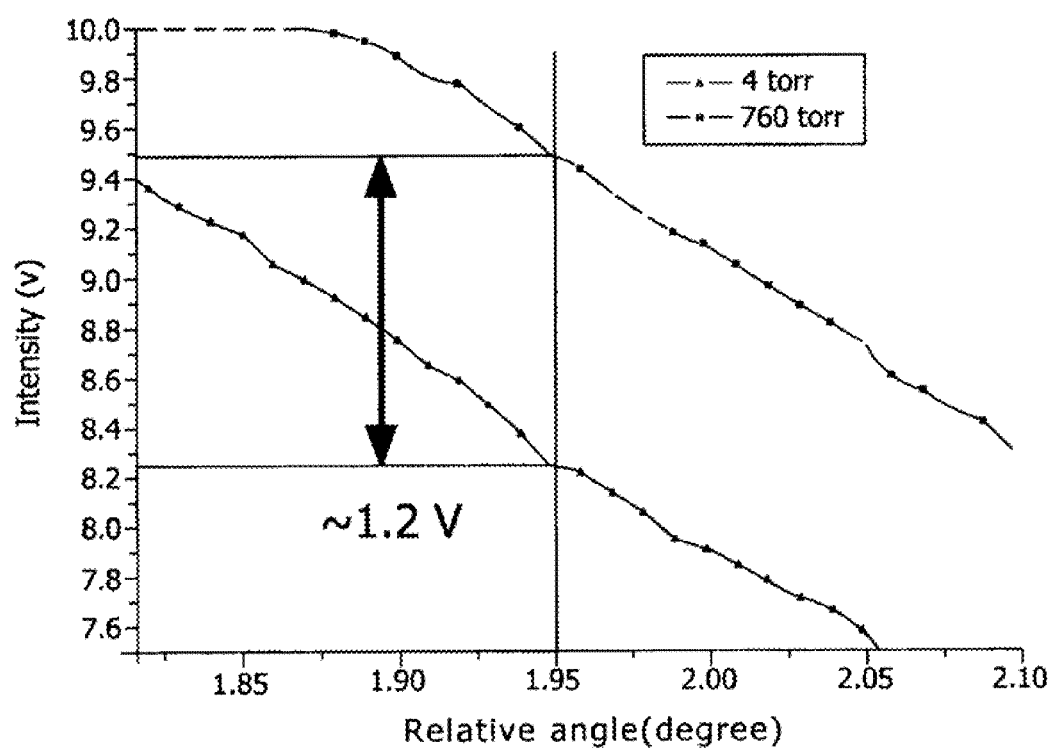
FIG. 5 shows the measured values using the principle of a novel measurement method.

The resonance curve for Fe-mesoporphyrin IX is graphed in FIG. 5, showing the resonance curves for angles measured by adjusting the atmospheric pressure around the sensor substrate to 4 torr and 760 torr. As such, the upper portions of the resonance curves are controlled to be saturated, so as to increase the angle slope. At the relative angle of about 1.95 degrees, the difference in voltage is determined to be about 1.2 V. While the sensor environment is made different, the resonance curves are measured at 4 torr and 760 torr. When a variation between two curves is the largest, there is the difference in voltage of about 1.2 V. The voltage is measured using the photodiode, and indicates the amount of light. FIGS. 4 and 5 illustrate the function of the oxygen sensor depending on the oxygen concentration, thus checking the change in the oxygen percentage in a predetermined chamber.

Next, the measurement system is mounted at the fixed angle, and the voltage is measured while controlling the oxygen concentration around the sensor substrate. Specifically, the change in amount of light (change in voltage) is measured at the fixed angle (which is previously determined as a position where the voltage change is large). The voltage thus measured is seen to be almost linear depending on the concentration.

Figure 6:
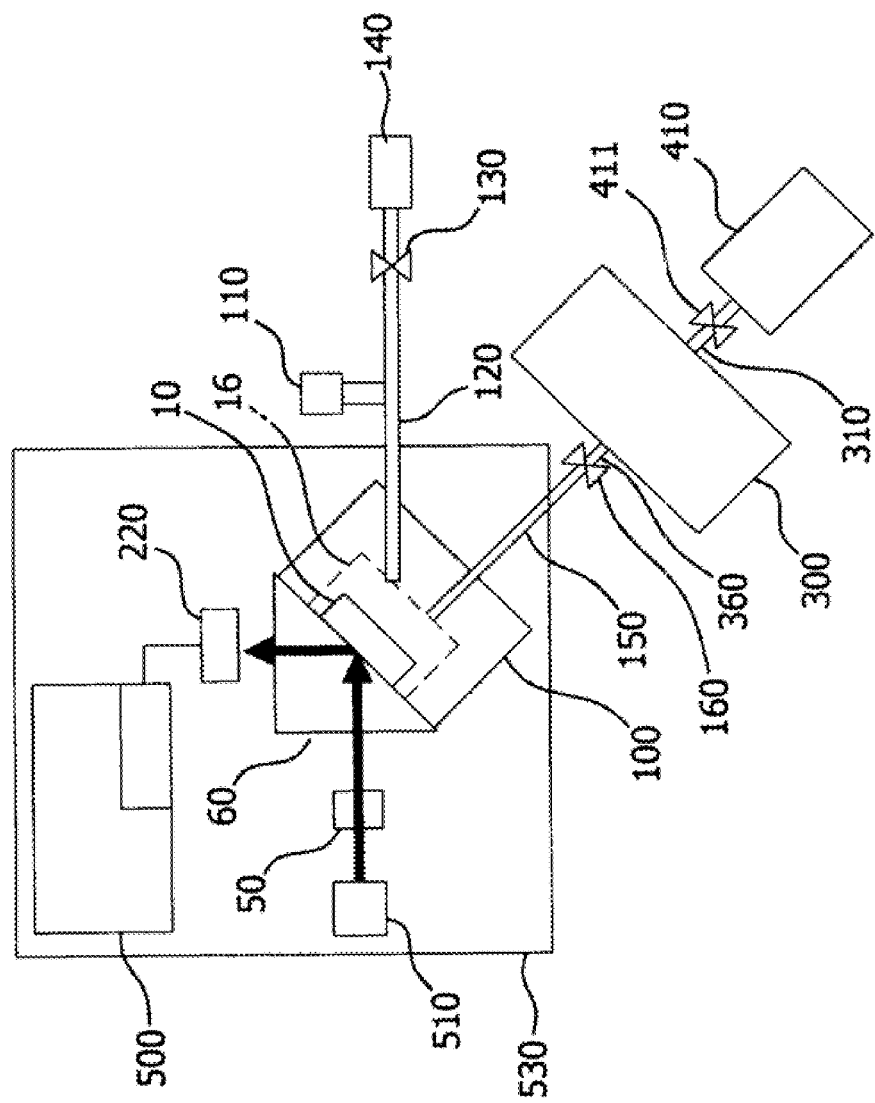
FIG. 6 schematically shows a small-sized OTR measurement system to which the novel measurement method is applied.

The OTR measurement system to which the newly proposed measurement method is applied is schematically illustrated in FIG. 6. The system of FIG. 6 is configured similarly to the oxygen sensor of FIG. 1, but is different in terms of having neither the chopper nor the lock-in amplifier and is used to measure only reflectivity at the measurement angle as in FIG. 5. The ADC-embedded microcontroller unit 500 is used to analyze the measured amount of light and then convert it into an oxygen concentration value. Briefly, the voltage measured using the photodiode is converted into the oxygen concentration. The photodiode 220 plays a role in measuring the amount of light to convert it into voltage. The laser diode 510 emits a laser. The measurement chamber guide 100 is a space for changing the state (oxygen concentration) around the material.

Figure 2:
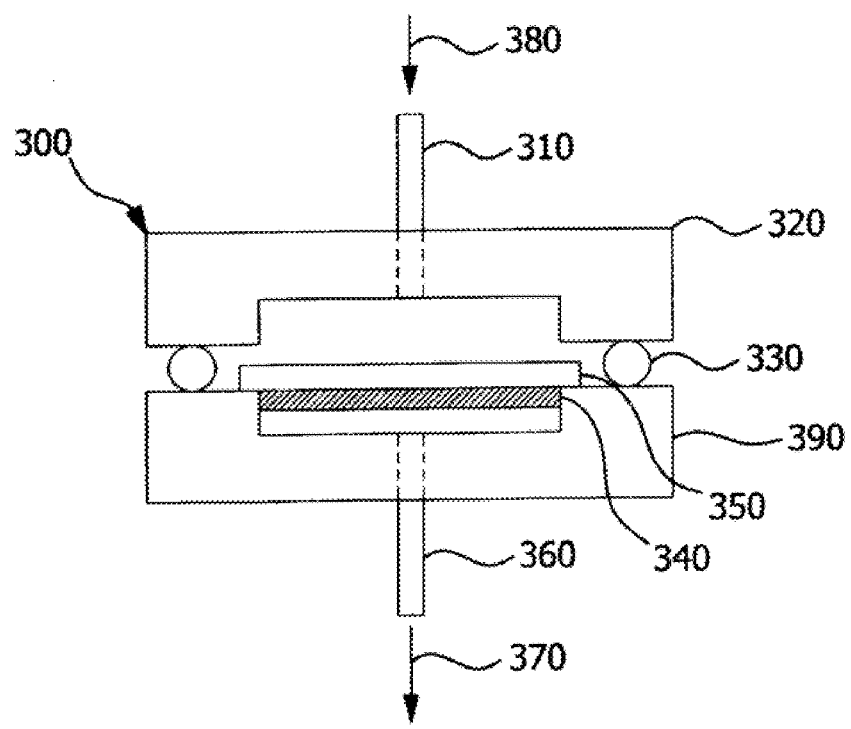
FIG. 2 schematically shows a sample mounting device which is a part of an OTR measurement system and is connected to the oxygen sensor.

Also, the sample mounting device 300, which is a part of the OTR measurement system and is connected to the oxygen sensor 530, is schematically shown in FIG. 2.

In FIG. 6, the oxygen sensor 530 may be driven using the IC type controller able to measure the input voltage of the light source without the use of a driver for analysis of wavelength or rotation of angle, and thus, the measurement system may be small in size. To determine the absolute concentration using the system of the present invention, the oxygen concentration conditions of 1%, 5%, 10% and 15% are made, and the voltage is measured using the photodiode, thus first determining a correlation of the measured voltage with respect to the actual concentration. The measured voltage values with respect to the actual concentration are stored in the microcontroller unit. Then, the absolute concentration of oxygen is determined from the voltage measured using the photodiode 220.

Next, the OTR is determined. To this end, first, the measurement chamber 16 of the oxygen sensor is evacuated using a vacuum pump 140. While oxygen supplied from an oxygen gas supplier 410 is passed through a sample mounting device 300, only a small amount of oxygen is introduced to the oxygen sensor 530. Using the results of FIG. 5, the voltage of the oxygen sensor is measured over time, thus determining the OTR. The output value of the oxygen sensor is measured to be the voltage, which is a value varying depending on the oxygen concentration around the sensor material. Using this voltage, the OTR is measured. The OTR is the amount of oxygen transmitted per unit area per unit time, and is typically represented by $cc/m^2/day$. The voltage of FIG. 4 or 5 is measured using the photodiode of the system of FIG. 6 at t1. The voltage values are measured at t1 and t2 using the photodiode, and such a difference in voltage is referred to as a voltage change. In order to determine an oxygen concentration change (%), the voltage thus obtained is multiplied by a calibration factor corresponding to the voltage change (V)/ oxygen concentration change (%). Thereby the oxygen concentration change (%) may be obtained at t1 and t2. The oxygen change (cc) results from multiplying the oxygen concentration change (%) by a conversion factor upon unit conversion (%→cc).

Oxygen change (cc)=(voltage change)*calibration coefficient

The calibration coefficient is calibration factor*conversion factor, and is a value which is calibrated and unit converted after the experiment. The calibration factor of the calibration coefficient is determined as follows. Specifically, 20% of FIG. 4 corresponds to 760 torr of FIG. 5, and 0.2% of FIG. 4 corresponds to 4 torr of FIG. 5. Thus, for example, when the angle is fixed and the time is t1, the voltage is measured to be about 9.5 V, and after a predetermined time, at t2, the voltage is measured to be about 8.3 V. The oxygen concentration is about 20% at t1, and is about 0.2% at t2. From the difference in voltage (9.5 V–8.3 V)/(20%–0.2%), the voltage per concentration may be determined, which indicates the correlation of measured voltage per oxygen concentration, called the calibration factor. However, the measured value is not valid (due to variation depending on measurement circumferences and conditions), and thus the calibration factor should be determined. As such, the experiment should be performed by accurately controlling the amount of oxygen. For an accurate calibration, the calibration coefficient usable in each oxygen sensor should be determined using an oxygen concentration controller ranging from 100% oxygen to 0% oxygen.

The OTR is represented as below.

OTR=oxygen change (cc)/converted area/converted time difference.

As described above, the present invention provides an oxygen sensor using the principle of SPR and an OTR measurement system including the same. According to the present invention, SPR which is proved is employed, so that measurement reliability can be ensured, and the concentration of only oxygen in a gas can be measured in real time. Also, because an oxygen-sensitive organic material is used, the oxygen sensor can be produced at low cost. In addition, the OTR measurement system including this sensor enables the selective measurement of only oxygen in a gas mixture, thus simplifying the entire construction thereof while obviating a need for an oxygen transmission film or an additional device for indirect measurement. Compared to conventional SPR measurement methods, in the present invention, angle change and wavelength analysis are not required, thus shortening the SPR measurement time and reducing the size of the system. Furthermore, this system is easily utilized in vacuum equipment in such a way that a window of the vacuum equipment is replaced with a prism used in the measurement of SPR, thus measuring the concentration of oxygen from outside the vacuum equipment.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An oxygen sensor using a principle of surface plasmon resonance, comprising:
    a laser diode that emits light;
    a polarizer that converts light emitted from the laser diode into polarized light;
    a prism that receives the polarized light from the polarizer and that has a sensor substrate provided on one surface thereof to reflect the polarized light, the sensor substrate being coated with an oxygen-sensitive organic material;
    an oxygen concentration measurement chamber that encloses the sensor substrate wherein oxygen a concentration of which is to be measured is contained therein;
    a photodiode that measures an amount of light reflected from the prism; and
    a microcontroller unit that controls operation of the oxygen sensor and that calculates the concentration of oxygen,
    wherein the concentration of oxygen is determined using the microcontroller unit having values of absolute concentration corresponding to the amount of light measured using the photodiode, and the concentration of oxygen is measured in a state in which an incidence angle of the polarized light incident on the sensor substrate is fixed.

2. The oxygen sensor as set forth in claim 1, further comprising:
    a pressure measurement pipe, one side of which is connected to the oxygen concentration measurement chamber and another side of which is connected to a vacuum pump and which includes a pressure gauge provided on an upper surface thereof and a vacuum pump valve disposed between the pressure gauge and the vacuum pump; and
    a gas input pipe, one side of which is connected to the oxygen concentration measurement chamber and another side of which is connected to a gas input valve.

3. The oxygen sensor as set forth in claim 1, further comprising a measurement chamber guide disposed to enclose the oxygen concentration measurement chamber.

4. The oxygen sensor as set forth in claim 1, wherein the sensor substrate comprises:
    a dielectric substrate;
    a nano-metal layer including metal nanoparticles applied on the dielectric substrate; and
    an organic material layer formed by linking the organic material to the metal nanoparticles of the nano-metal layer.

5. The oxygen sensor as set forth in claim 1, wherein the sensor substrate comprises:
    a dielectric substrate;
    a nano-metal layer including a metal film applied on the dielectric substrate; and
    an organic material layer formed on the nano-metal layer.

6. The oxygen sensor as set forth in claim 4, wherein the organic material is responsible for either or both of adsorption and desorption of oxygen gas.

7. The oxygen sensor as set forth in claim 4, wherein the organic material comprises a metal-porphyrin or hemoglobin which is selectively sensitive to only oxygen.

8. The oxygen sensor as set forth in claim 4, wherein the metal nanoparticles have a diameter ranging from 1 nm to 99 nm.

9. The oxygen sensor as set forth in claim 4, wherein the dielectric substrate comprises glass.

10. The oxygen sensor as set forth in claim 5, wherein the metal film has a thickness ranging from 1 nm to 99 nm.

11. The oxygen sensor as set forth in claim 5, wherein the organic material is responsible for either or both of adsorption and desorption of oxygen gas.

12. The oxygen sensor as set forth in claim 5, wherein the organic material comprises a metal-porphyrin or hemoglobin which is selectively sensitive to only oxygen.

13. The oxygen sensor as set forth in claim 5, wherein the dielectric substrate comprises glass.

14. An oxygen transmission rate measurement system comprising an oxygen sensor using a principle of surface plasmon resonance, the oxygen transmission rate measurement system comprising:
    the oxygen sensor, including:
        a laser diode that emits light;
        a polarizer that converts light emitted from the laser diode into polarized light;
        a prism that receives the polarized light from the polarizer and that has a sensor substrate provided on one surface thereof to reflect the polarized light, the sensor substrate being coated with an oxygen-sensitive organic material;
        an oxygen concentration measurement chamber that encloses the sensor substrate wherein oxygen a concentration of which is to be measured is contained therein,
        a photodiode that measures an amount of light reflected from the prism, and
        a microcontroller unit that controls operation of the oxygen sensor and that calculates an oxygen concentration change and an oxygen transmission rate; and
    an oxygen supplier connected to one side of the oxygen sensor that supplies oxygen gas,
    wherein the oxygen transmission rate is measured by determining the oxygen concentration change from the amount of the light measured using the photodiode at predetermined temporal intervals.

15. The oxygen transmission rate measurement system as set forth in claim 14, wherein the organic material is responsible for either or both of adsorption and desorption of oxygen gas.

16. The oxygen transmission rate measurement system as set forth in claim 14, wherein the organic material comprises a metal-porphyrin or hemoglobin which is selectively sensitive to only oxygen.

17. The oxygen transmission rate measurement system as set forth in claim 14, wherein the sensor substrate comprises:
   a dielectric substrate;
   a nano-metal layer including metal nanoparticles applied on the dielectric substrate; and
   an organic material layer formed by linking the organic material to the metal nanoparticles of the nano-metal layer.

18. The oxygen transmission rate measurement system as set forth in claim 14, wherein the sensor substrate comprises:
   a dielectric substrate;
   a nano-metal layer including a metal film applied on the dielectric substrate; and
   an organic material layer formed on the nano-metal layer.

19. The oxygen transmission rate measurement system as set forth in claim 14, wherein the oxygen supplier comprises:
   a gas input pipe one side of which is connected to the oxygen concentration measurement chamber and another side of which is connected to a gas input valve;
   a sample mounting device one side of which is connected to the gas input valve and another side of which is connected to an oxygen supply valve; and
   an oxygen gas supplier one side of which is connected to the oxygen supply valve.

20. The oxygen transmission rate measurement system as set forth in claim 17, wherein the metal nanoparticles have a diameter ranging from 1 nm to 99 nm.

21. The oxygen transmission rate measurement system as set forth in claim 17, wherein the dielectric substrate comprises glass.

22. The oxygen transmission rate measurement system as set forth in claim 18, wherein the metal film has a thickness ranging from 1 nm to 99 nm.

23. The oxygen transmission rate measurement system as set forth in claim 18, wherein the dielectric substrate comprises glass.

24. The oxygen transmission rate measurement system as set forth in claim 19, wherein the organic material is responsible for either or both of adsorption and desorption of oxygen gas.

25. The oxygen transmission rate measurement system as set forth in claim 19, wherein the organic material comprises a metal-porphyrin or hemoglobin which is selectively sensitive to only oxygen.

26. The oxygen transmission rate measurement system as set forth in claim 19, wherein the sensor substrate comprises:
   a dielectric substrate;
   a nano-metal layer including metal nanoparticles applied on the dielectric substrate; and
   an organic material layer formed by linking the organic material to the metal nanoparticles of the nano-metal layer.

27. The oxygen transmission rate measurement system as set forth in claim 19, wherein the sensor substrate comprises:
   a dielectric substrate;
   a nano-metal layer including a metal film applied on the dielectric substrate; and
   an organic material layer formed on the nano-metal layer.

28. The oxygen transmission rate measurement system as set forth in claim 26, wherein the metal nanoparticles have a diameter ranging from 1 nm to 99 nm.

29. The oxygen transmission rate measurement system as set forth in claim 26, wherein the dielectric substrate comprises glass.

30. The oxygen transmission rate measurement system as set forth in claim 27, wherein the metal film has a thickness ranging from 1 nm to 99 nm.

31. The oxygen transmission rate measurement system as set forth in claim 27, wherein the dielectric substrate comprises glass.

* * * * *